United States Patent
Smith

(10) Patent No.: US 9,506,337 B2
(45) Date of Patent: Nov. 29, 2016

(54) SYSTEM AND METHOD FOR IMPROVED CUTTINGS MEASUREMENTS

(75) Inventor: Adrian E. Smith, Rochdale Lanes (GB)

(73) Assignee: Halliburton Energy Services, Inc., Houston, TX (US)

( * ) Notice: Subject to any disclaimer, the term of this patent is extended or adjusted under 35 U.S.C. 154(b) by 198 days.

(21) Appl. No.: 14/370,112

(22) PCT Filed: Jan. 9, 2012

(86) PCT No.: PCT/US2012/020663
§ 371 (c)(1),
(2), (4) Date: Jul. 1, 2014

(87) PCT Pub. No.: WO2013/105930
PCT Pub. Date: Jul. 18, 2013

(65) Prior Publication Data
US 2015/0013448 A1    Jan. 15, 2015

(51) Int. Cl.
*E21B 44/02* (2006.01)
*E21B 47/01* (2012.01)
*E21B 45/00* (2006.01)
*E21B 44/04* (2006.01)
*E21B 49/00* (2006.01)
*E21B 21/06* (2006.01)
*G01N 3/58* (2006.01)
*B07B 13/16* (2006.01)

(52) U.S. Cl.
CPC .............. *E21B 44/04* (2013.01); *E21B 21/066* (2013.01); *E21B 47/01* (2013.01); *E21B 49/005* (2013.01); *G01N 3/58* (2013.01); *B07B 13/16* (2013.01)

(58) Field of Classification Search
CPC ...... E21B 44/04; E21B 47/01; E21B 49/005; E21B 21/066; E21B 21/01; B07B 13/16
USPC ....................................................... 73/152.46
See application file for complete search history.

(56) References Cited

U.S. PATENT DOCUMENTS

| 4,413,511 A | 11/1983 | Godbey |
| 4,809,791 A | 3/1989 | Hayatdavoudi |
| 5,205,164 A | 4/1993 | Steiger et al. |
| 5,240,324 A | 8/1993 | Phillips et al. |
| 5,285,692 A | 2/1994 | Steiger et al. |
| 6,003,834 A | 12/1999 | Read |
| 6,176,323 B1 | 1/2001 | Weirich et al. |
| 6,308,787 B1 | 10/2001 | Alft |

(Continued)

OTHER PUBLICATIONS

International Search Report mailed Sep. 24, 2012 which issued in corresponding International Patent Application No. PCT/US2012/020663 (5 pages).

(Continued)

*Primary Examiner* — Walter L Lindsay, Jr.
*Assistant Examiner* — Ruth Labombard
(74) *Attorney, Agent, or Firm* — Chamberlain, Hrdlicka

(57) ABSTRACT

A method and system for improving cuttings measurements in drilling operations includes rotating a helical screw in a trough at a first speed, measuring a first weight of a cuttings mixture within the trough, measuring a first torque required to maintain rotation of the helical screw at the first speed through the cuttings mixture, and calculating a difference between the first torque and a second torque required to maintain rotation of the helical screw at the first speed through a second weight of natural cuttings equal to the first weight.

19 Claims, 7 Drawing Sheets

(56) References Cited

U.S. PATENT DOCUMENTS

| | | |
|---|---|---|
| 6,321,860 B1 | 11/2001 | Reddoch |
| 6,386,026 B1 | 5/2002 | Zamfes |
| 6,410,862 B1 | 6/2002 | Lecann |
| 6,640,912 B2 | 11/2003 | Reddoch |
| 6,662,884 B2 | 12/2003 | Hemphill |
| 6,665,636 B1 | 12/2003 | Allouche et al. |
| 6,823,238 B1 | 11/2004 | Hensley et al. |
| 6,986,396 B2 | 1/2006 | Hemphill |
| 7,044,237 B2 | 5/2006 | Leuchtenberg |
| 7,134,353 B2 | 11/2006 | Fout et al. |
| 7,278,496 B2 | 10/2007 | Leuchtenberg |
| 7,367,411 B2 | 5/2008 | Leuchtenberg |
| 7,642,474 B2 | 1/2010 | Calleri |
| 7,650,950 B2 | 1/2010 | Leuchtenberg |
| 7,677,332 B2 | 3/2010 | Spiecker et al. |
| 2003/0159310 A1 | 8/2003 | Hensley et al. |
| 2006/0020390 A1 | 1/2006 | Miller |
| 2008/0196942 A1 | 8/2008 | Bingham et al. |
| 2009/0194330 A1 | 8/2009 | Gray |
| 2010/0038143 A1 | 2/2010 | Burnett et al. |
| 2010/0116553 A1 | 5/2010 | Spiecker et al. |
| 2010/0193249 A1 | 8/2010 | Saiz |

OTHER PUBLICATIONS

International Written Opinion mailed Sep. 24, 2012 which issued in corresponding International Patent Application No. PCT/US2012/020663 (3 pages).

SYSTEM AND METHOD FOR IMPROVED CUTTINGS MEASUREMENTS

CROSS-REFERENCE AND CLAIM OF PRIORITY TO RELATED APPLICATION

This application is a U.S. National Phase of International Application No. PCT/US2012/020663, which was filed on Jan. 9, 2012, and is incorporated herein by reference in its entirety and for all purposes.

FIELD OF THE INVENTION

The present disclosure relates generally to oilfield measurements, and more particularly, to systems and methods for improved cuttings measurements.

BACKGROUND OF THE INVENTION

Boreholes are created by drilling into the earth using a rig. The rig drives a bottomhole assembly (BHA) on a drill string to create a hole. The BHA comprises a drill bit, which is provided with sufficient weight-on-bit (WOB) to break the rock. The BHA also may provide directional control of the drill bit and may use sensors to take downhole measurements of actual drilling conditions.

Drilling fluid or drilling mud is pumped downhole through a drill pipe while drilling. The drilling fluid cools the drill bit, circulates through the borehole, and returns drill cuttings, such as sand and shale, to the surface. The cuttings are passed through a shaker which strains the cuttings from the drilling fluid, and optionally, through a centrifuge which separates cuttings such as sand from the drilling fluid. The cleaned drilling fluid is then returned downhole through the drill pipe.

DETAILED DESCRIPTION

Systems and methods for improved cuttings measurements are described. In the following description, for purposes of explanation, numerous specific details are set forth in order to provide a thorough understanding of the exemplary embodiments. It is apparent to one skilled in the art, however, that embodiments of the present invention can be practiced without these specific details or with an equivalent arrangement. In some instances, well-known structures and devices are shown in block diagram form in order to avoid unnecessarily obscuring the embodiments.

As described herein, some embodiments of the invention obtain real-time, constant measurements of the amount of cuttings coming over shakers, corrected in real-time for the amount of drilling fluid carrying these cuttings. These measurements can be compared to values calculated using sophisticated lab tables, such as volumetric lag tables produced by the InSite® software package from Halliburton Energy Services Inc., that indicate a theoretical or predicted amount of cuttings created at the bit and that should be measured at the shakers. According to some embodiments, alarms can be activated to alert operators when a measured amount of cuttings differs from a predicted amount of cuttings by more than a threshold amount.

Figure 1:
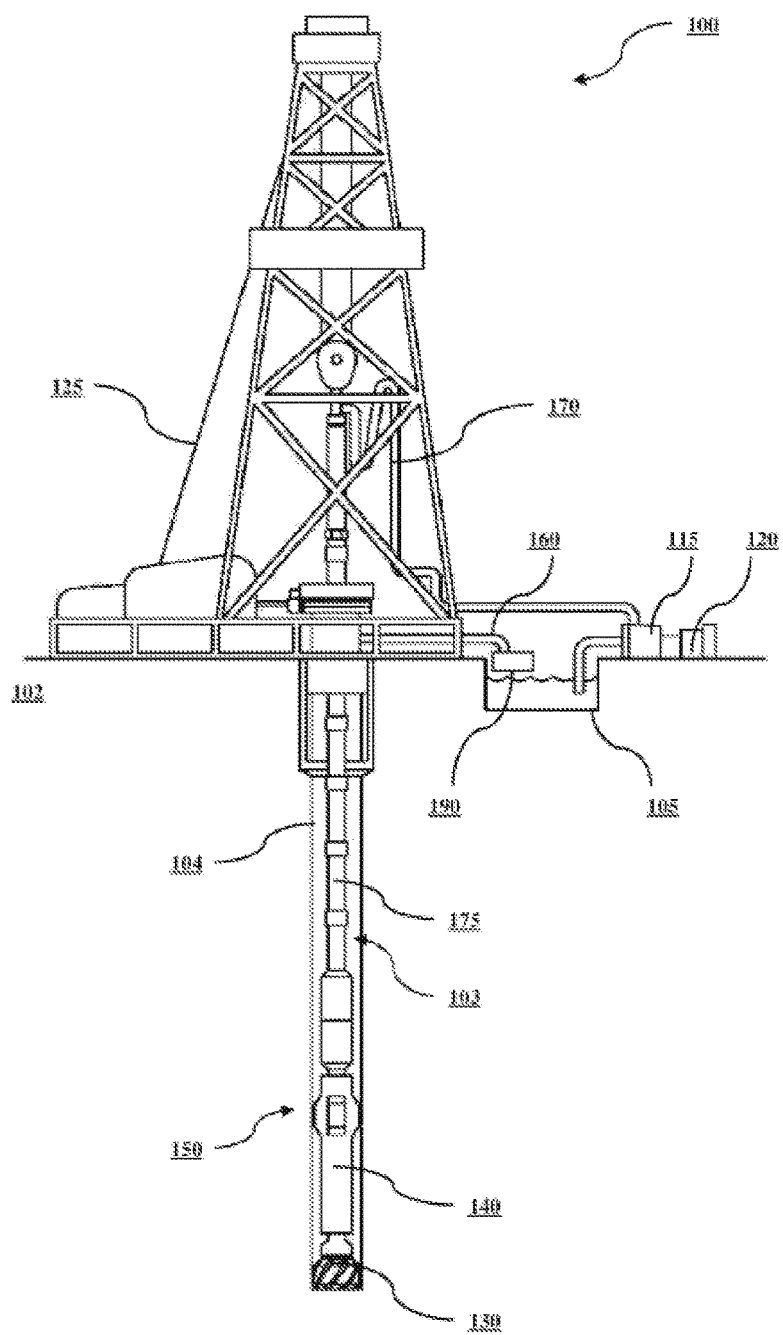
FIG. 1 illustrates a rotary drilling rig according to an embodiment of the invention.

Referring now to the drawings, FIG. 1 illustrates an exemplary rotary drilling rig 100 that can be employed in concert with embodiments of the invention. Boreholes can be created by drilling into the earth using drilling rig 100. Rig 100 drives a bottom hole assembly (BHA) 150, positioned at the bottom of drill string 175, into earth 102. According to some embodiments, the BHA 150 comprises a drill bit 130 and tool string 140, which can be moved up and down within a hole as facilitated by drill line 125. An annulus 103 is formed between the drill string 175 and the sides 104 of the hole. The drill bit 130 is provided with sufficient weight-on-bit (WOB) and torque to create the hole. According to some embodiments, the BHA 150 also provides directional control of drill bit 130. According to some embodiments, the tool string 140 can be semi-permanently mounted with measurement tools (not shown), such as measurement-while-drilling (MWD) and logging-while-drilling (LWD) tools, that take downhole measurements of drilling conditions, as described further herein. According to some embodiments, the measurement tools are self-contained within tool string 140, as shown in FIG. 1.

Drilling fluid (such as mud, in this example) is pumped downhole from a mud tank 105 by a mud pump 115 (powered by a power source 120) through a stand pipe 170. The mud cools the drill bit 130, circulates through annulus 103, and returns drill cuttings, such as sand and shale, to the surface. The cuttings and mud mixture is passed through a flow line 160 and into a trough system 190, including shakers and an optional centrifuge (not shown). The trough system 190 is described in greater detail with respect to FIGS. 3, 4A and 4B herein. The shakers separate a majority of solids, such as cuttings and fines, from the mud. Cleaned mud is then returned downhole through the stand pipe 170. Changes in various factors, such as change in rate of penetration (ROP) or formation, can be observed, analyzed and accounted for during this process. Although referenced herein for convenience as "mud," the term "mud" can refer to both mud alone and a mud/cuttings mixture. Further, although referenced herein as "drilling fluid," the term "drilling fluid" can refer to both drilling fluid alone and a drilling fluid and cuttings mixture.

Although shown and described with respect to a rotary drill system in FIG. 1, many types of drills can be employed in carrying out embodiments of the invention, such as, for example, Auger drills, air core drills, cable tool drills, diamond core drills, percussion rotary air blast (RAB) drills, reverse circulation drills, and the like. Drills and drill rigs used in embodiments of the invention can be used onshore (as shown and described with respect to FIG. 1), or offshore (not shown). Offshore oil rigs that can be used in accordance with embodiments of the invention include, for example, floaters, fixed platforms, gravity-based structures, drillships, semi-submersible platform, jack-up drilling rigs, tension-leg platforms, and the like. Embodiments of the invention can be applied to rigs ranging anywhere from small in size and portable, to bulky and permanent.

Further, although described herein with respect to oil drilling, embodiments of the invention can be used in many other applications. For example, disclosed methods can be used in drilling for mineral exploration, environmental investigation, natural gas extraction, underground installation, mining operations, water wells, geothermal wells, and the like.

Figure 2:
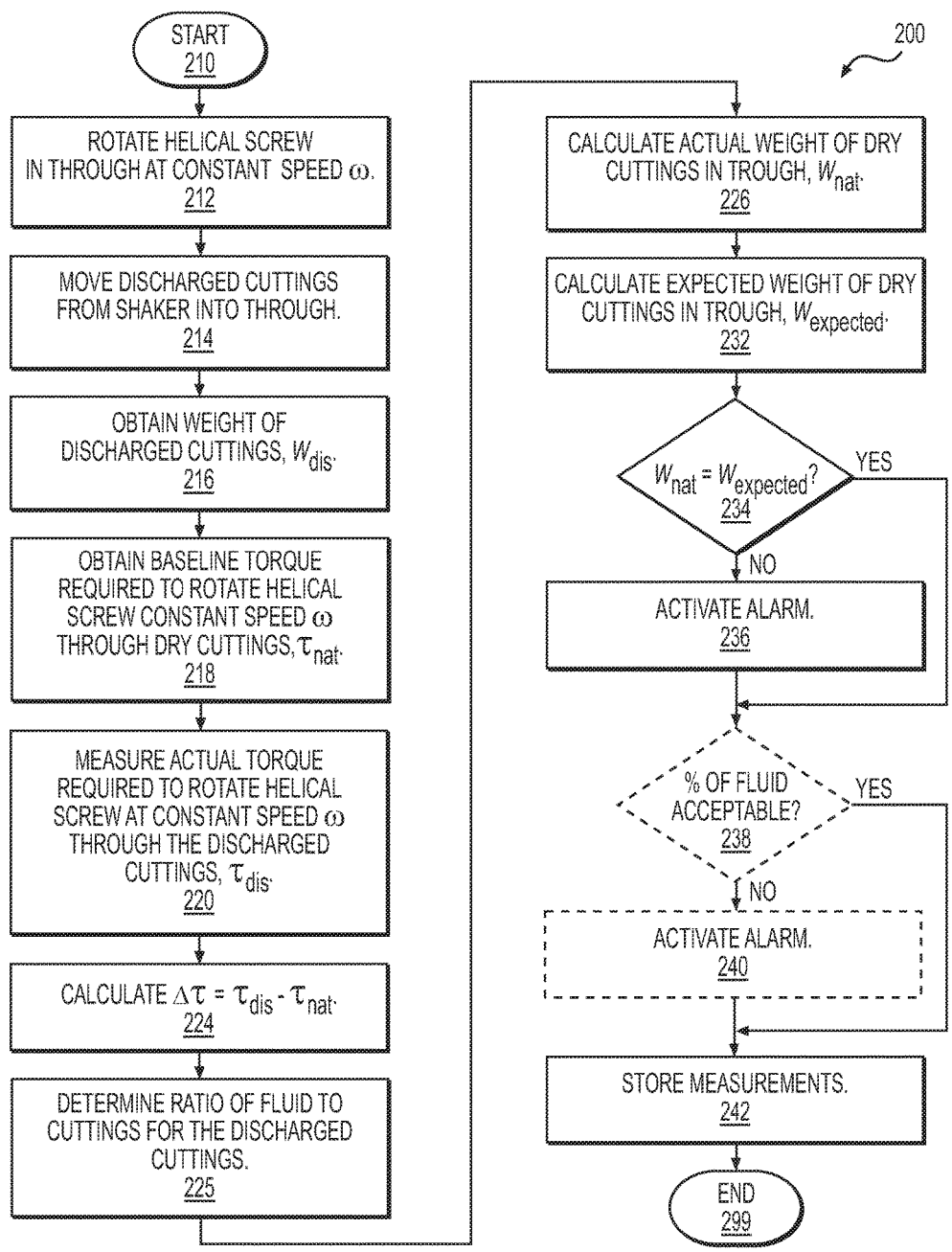
FIG. 2 is a flowchart illustrating the acts of a method for improved cuttings measurements according to an embodiment of the invention.

FIG. 2 is a flowchart 200 illustrating a process for improved cuttings measurements according to an embodiment of the invention. The process begins at 210, at which point a cuttings and drilling fluid mixture is returned to the surface through the annulus, and moved into one or more shakers. The cuttings and drilling fluid mixture can be moved into the shaker by a flow line, for example, such as flow line 160 of FIG. 1. The shakers (and optionally, a centrifuge) separate the majority of solids, such as cuttings and fines, from the drilling fluid. The cleaned drilling fluid is returned downhole by a stand pipe, for example, such as stand pipe 170 of FIG. 1.

At 212, a helical screw within a trough is rotated at a constant speed ω. Although illustrated as occurring at a particular position within the method, it is understood that the helical screw can begin rotation at a number of different times within the method while still allowing for proper measurement of the torque required to maintain its rotation through the cuttings.

The discharge from the shakers, or the "discharged cuttings", are moved into the trough at 214. Although the cuttings and drilling fluid mixture has been substantially separated by the shakers, it is understood that an amount of drilling fluid may remain on the surface of the discharged cuttings, within depressions or holes in the discharged cuttings, between discharged cuttings, or absorbed into the discharged cuttings.

At 216, the weight of the discharged cuttings, $w_{dis}$, is obtained. The weight of the discharged cuttings can be obtained by measuring the discharged cuttings independently, measuring the discharged cuttings within the trough, or measuring the discharged cuttings on or within any other component having a known weight. For example, the total weight of the trough system can be measured by weight sensors below or suspending the trough. The weight of the discharged cuttings can then be determined by subtracting the weight of the trough, helical screw, and any other non-cuttings and non-drilling fluid components attached to the trough, from the total measured weight of the trough system.

As discussed further herein, a pre-determined graph, chart or equation illustrating a known amount of torque required to maintain a constant rotation ω of the helical screw through various weights of natural cuttings is established. At 218, a baseline torque, $\tau_{nat}$, required to rotate the helical screw through the weight of the discharged cuttings, $w_{dis}$, is obtained from the graph, chart or equation. Thus, the baseline torque $\tau_{nat}$ represents the torque that would be required to rotate the helical screw through the discharged cuttings if the discharged cuttings were natural, i.e., entirely free of drilling fluid. The word "natural" is used herein to describe cuttings that are completely separated from the drilling fluid. However, it is contemplated that such natural cuttings are not necessarily "dry", as ordinary pore water may be present in cuttings free of drilling fluid. Thus, the phrase "natural cuttings" could refer to any cuttings separate from the drilling fluid, with or without pore water.

At 220, the actual torque, $\tau_{dis}$, required to maintain rotation of the helical screw through the discharged cuttings at the constant speed ω, is measured. The actual torque, $\tau_{dis}$, can be measured by a variety of gauges, sensors or meters, such as a torque meter coupled to a motor driving the helical screw, as discussed further herein. At 224, the difference $\Delta\tau$ between the actual torque and the baseline torque is determine by the equation $\Delta\tau = \tau_{dis} - \tau_{nat}$. This difference $\Delta\tau$ represents the difference in torque required to maintain rotation of the helical screw at the constant speed ω due to the presence of fluid on the discharged cuttings as compared to natural cuttings.

A pre-determined graph, chart or equation illustrating a known ratio or percentage of fluid to cuttings based on a difference in torque $\Delta\tau$ is consulted to determine the particular ratio or percentage of drilling fluid to cuttings for the discharged cuttings at 225. At 226, this ratio is used to isolate the weight of the natural cuttings (i.e., cuttings without any drilling fluid), $w_{nat}$, in the trough. For example, the weight of the natural cuttings $w_{nat}$ can be determined through multiplication of the percentage of cuttings in the discharge by the total weight of the discharged cuttings, $w_{dis}$.

The expected volume of natural cuttings being discharged into the trough, $V_{expected}$, is obtained from volumetric lag tables, such as those produced by the InSite® software package from Halliburton Energy Services Inc. Such volumes can be predicted based upon geology, weight-on-bit (WOB), drilling speed, downhole conditions, and various other specifications. The density of the discharged cuttings, $\rho_{dis}$, can be estimated from historical density data or supplied by MWD/LWD tools, for example. The expected weight of natural cuttings being discharged into the trough, $w_{expected}$, can then be calculated using the equation $w_{expected} = V_{expected} \times \rho_{dis}$, at 232.

At 234, the weight of the natural cuttings in the trough, $w_{nat}$, is compared to the expected weight of natural cuttings being discharged into the trough, $w_{expected}$. If the weight of the natural cuttings in the trough, $w_{nat}$, is not within an established acceptable threshold of the expected weight of natural cuttings being discharged into the trough, $w_{expected}$, an alarm is activated at 236 according to the illustrated embodiment, and the process proceeds to optional decision block 238 (or directly to 240). If the weight of the natural cuttings in the trough, $w_{nat}$, is indeed within an established acceptable threshold of the expected weight of natural cuttings being discharged into the trough, $w_{expected}$, the process proceeds to optional decision block 238 (or directly to 240).

At optional decision block 238, the percentage of fluid on the discharged cuttings (determined at 225) is compared to an established acceptable percentage of fluid to be present on the discharged cuttings. At optional process block 240, an alarm is activated if the percentage of fluid exceeds the established acceptable percentage of fluid, and the process continues at 242. If the percentage of fluid is within the acceptable threshold, the process proceeds directly to 242. At 242, the various measurements, calculations and results are stored, and the process ends at 299.

According to some embodiments, corrective action can be taken based on an activated alarm and/or stored measurements. Corrective action can be taken manually, such as by an operator; automatically, such as in automated drilling systems; or a combination thereof. In combined embodiments, the automated system can identify one or more potential problems and select one or more corrective actions based on the type of the alarm, the stored measurements and/or any other downhole conditions or measurements. The automated system can identify the potential problem(s) and suggest the corrective action(s) to an operator, who must authorize the suggested action prior to implementation of the corrective action(s). Alternatively, if the operator disagrees with one or more of the proposed corrective action(s), the operator can modify the suggested action or deny the action entirely.

A notable difference between the actual and expected weights of natural cuttings within the trough may indicate that downhole conditions, i.e., geology, drilling depth, drilling speed, borehole size, etc., are not as expected. A higher than expected amount of cuttings could indicate that a bigger hole is being drilled than what was originally desired or intended. A lower than expected amount of cuttings could indicate that the cuttings are not being efficiently cleaned out of the hole, which could in turn cause the pipe to get stuck. In the latter case, the method of drilling could be changed to remedy the predicted problem. For example, in the case of horizontal drilling, the rotary speed can be increased to "clean" the hole, and/or a more viscous fluid can be pumped downhole. Numerous other problems and corrective actions can similarly be identified based on their particular surrounding circumstances and measurements.

A percentage of fluid on the discharged cuttings within the trough higher than an acceptable threshold could also indicate various problems. For example, a greater than expected amount of fluid could indicate an inefficiency of the shakers that could be corrected by various adjustments, such as changes to screen desk angle, vibration, G-force and cuttings conveyance velocity. Such adjustments would reduce costs by maximizing fluid reclamation. Further, drilling waste would be limited, lessening the economic impact of the meticulous processing, treatment and disposal required of discharged cuttings. Further, potentially adverse environmental effects caused by fluids retained on the cuttings would be limited.

Figure 3:
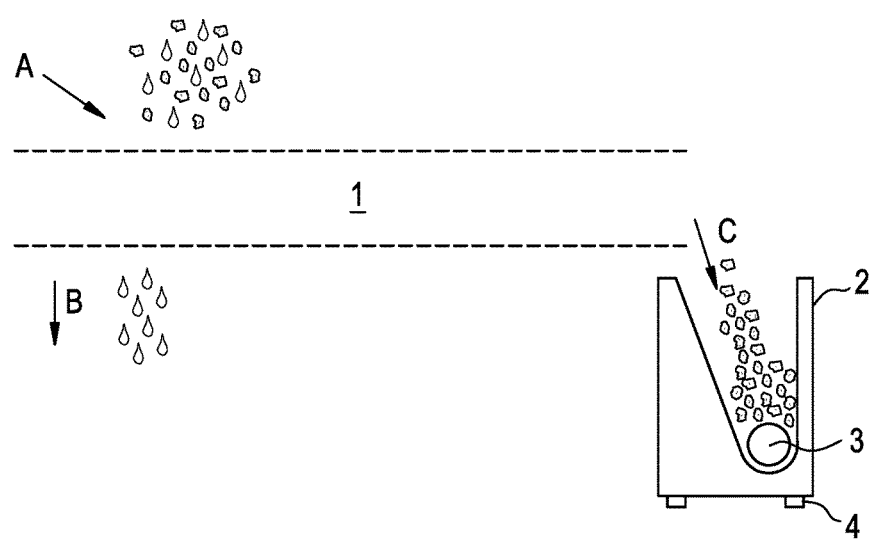
FIG. 3 is a plan view of a system for improved cuttings measurements according to an embodiment of the invention.
Figure 4A:
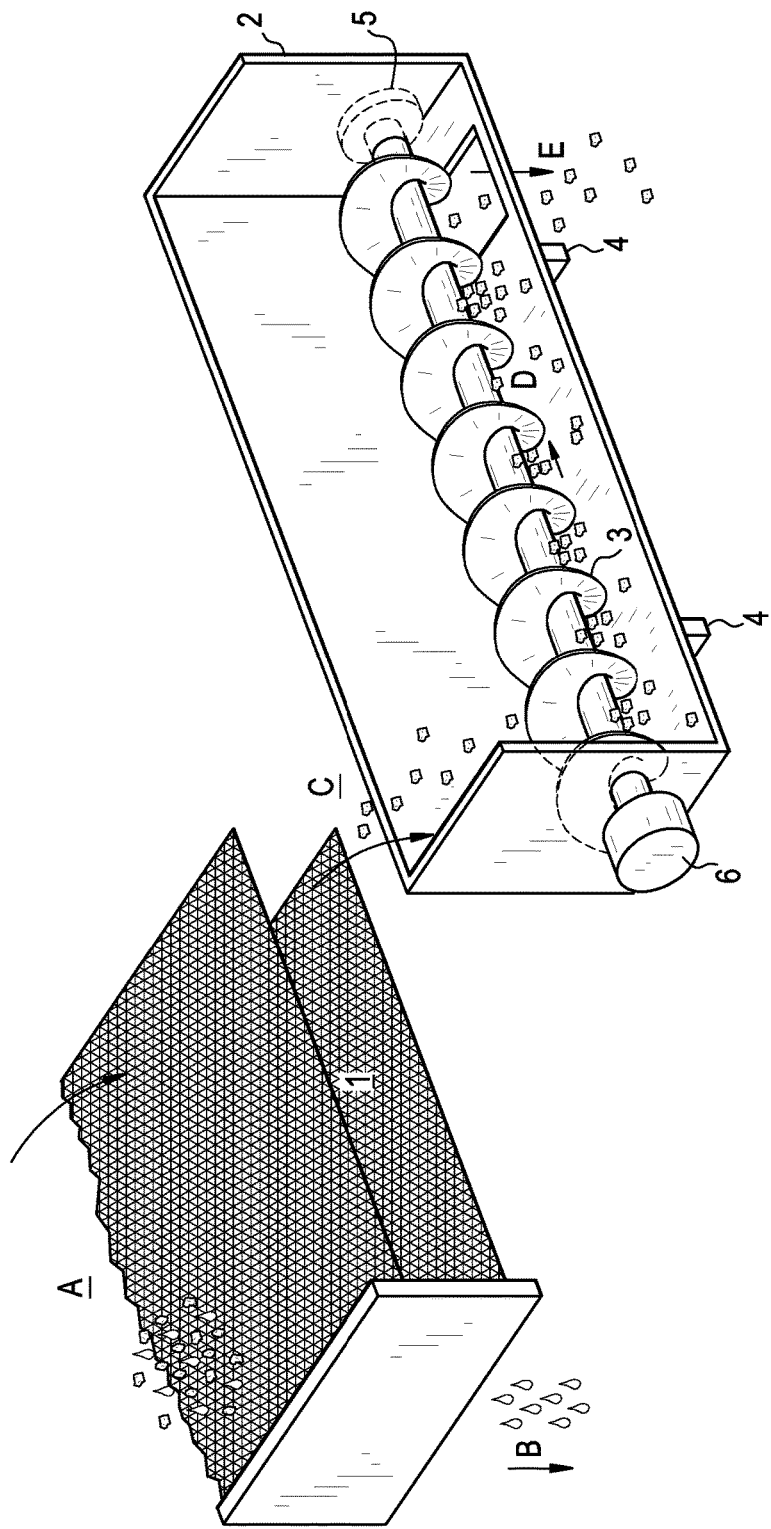
FIG. 4A is a perspective view of a system for improved cuttings measurements according to an embodiment of the invention.

FIGS. 3 and 4A illustrate exemplary trough systems for improved cuttings measurements that can be employed in concert with embodiments of the invention. As illustrated, a cuttings and drilling fluid mixture flows into shale shaker screens 1 at point A, for example. Shaker screens 1 allow the cleaned drilling fluid to flow out at point B, while discharging the cuttings into trough 2 at point C. Trough 2 comprises a helical screw 3 having a central shaft. According to some embodiments, helical screw 3 is rotationally secured with bearing 5, for example, to trough 2 (such as is shown in FIG. 4A, for example). Although illustrated and described with respect to bearing 5, however, it is understood that any means for rotationally coupling helical screw 3 to trough 2 can be used.

As further shown in FIGS. 4A, helical screw 3 is driven rotationally by motor 6. Motor 6 can be, for example, an electrical, hydraulic or pneumatic motor, and is preferably certified to work in areas near rig shale shakers. A constant speed controller (not shown) is used in conjunction with motor 6, and can be positioned either externally or internally to motor 6. The constant speed controller ensures that motor 6 drives helical screw 3 at an uninterrupted constant speed. Further, the constant speed controller or motor 6 can internally include a gauge, sensor or meter that identifies changes in torque or power needed by motor 6 to maintain constant rotation of helical screw 3, such as a torque meter. In another embodiment, a torque meter can be provided external to the constant speed controller or motor 6, whilst still being operatively coupled thereto.

Helical screw 3 continually moves the discharged cuttings falling into trough 2 in direction D, and discharges them from trough 2 at point E. Thus, according to some embodiments, the torque measurements described herein can be taken without interruption, as it is unnecessary to empty the cuttings out of trough 2 at regular intervals. By eliminating the need to empty trough 2, inaccuracies caused by estimating what the readings might have been during the time that trough 2 is emptied are eliminated. The torque or power required by the motor to maintain a constant rotation of the screw can therefore be measured in real-time, without interruption, and be continually sent to a computing device.

Weight sensors 4 under trough 2 can also take constant continuous, uninterrupted readings of the weight of the entire system, including the trough, helical screw and cuttings, and send the weight measurements to a computing device. Although shown and described with weight sensors 4 positioned under trough 2, it is understood that weight sensors 4 can take a reading of the weight at a variety of other positions, such as through suspension.

Figure 4B:
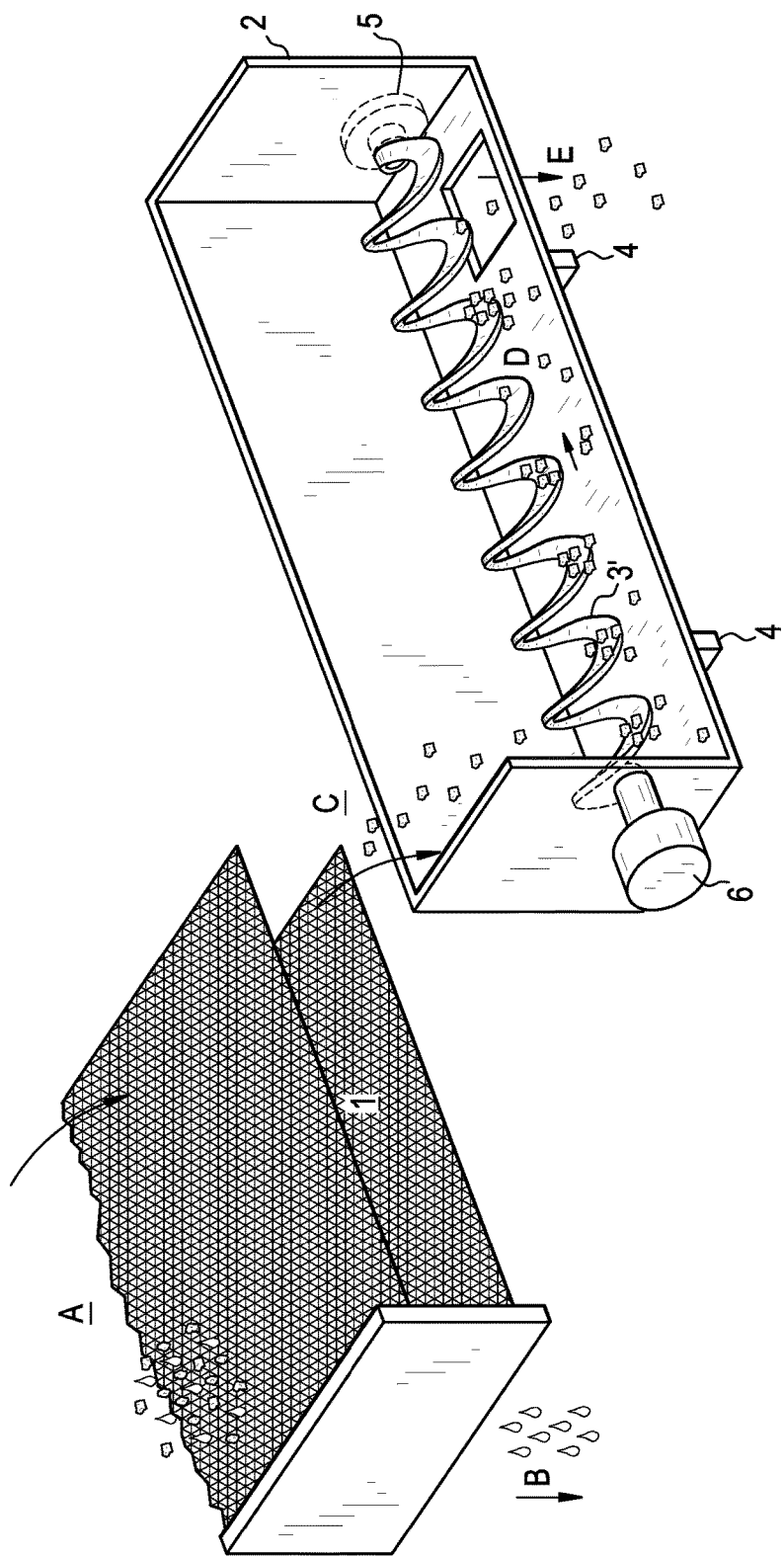
FIG. 4B is a perspective view of a system for improved cuttings measurements according to an embodiment of the invention.

FIG. 4B illustrates an alternative embodiment of an exemplary trough system for improved cuttings measurements. In this embodiment, trough 2 comprises a helical screw 3' having no central shaft. A configuration according to FIG. 4B performs similar functions to those described with respect FIGS. 3 and 4A. It is contemplated, however, that different advantages may be realized by the use of different embodiments. For example, a greater volume of cuttings may be held in trough 2 of FIG. 4B due to the lack of a central shaft, and less torque may be required to rotate the cuttings, which are not displaced by the central shaft. However, helical screw 3' may be less efficient at moving the same volume of cuttings as helical screw 3, because the cuttings may be able to more easily displace out of the path of movement in direction D.

Figure 5:
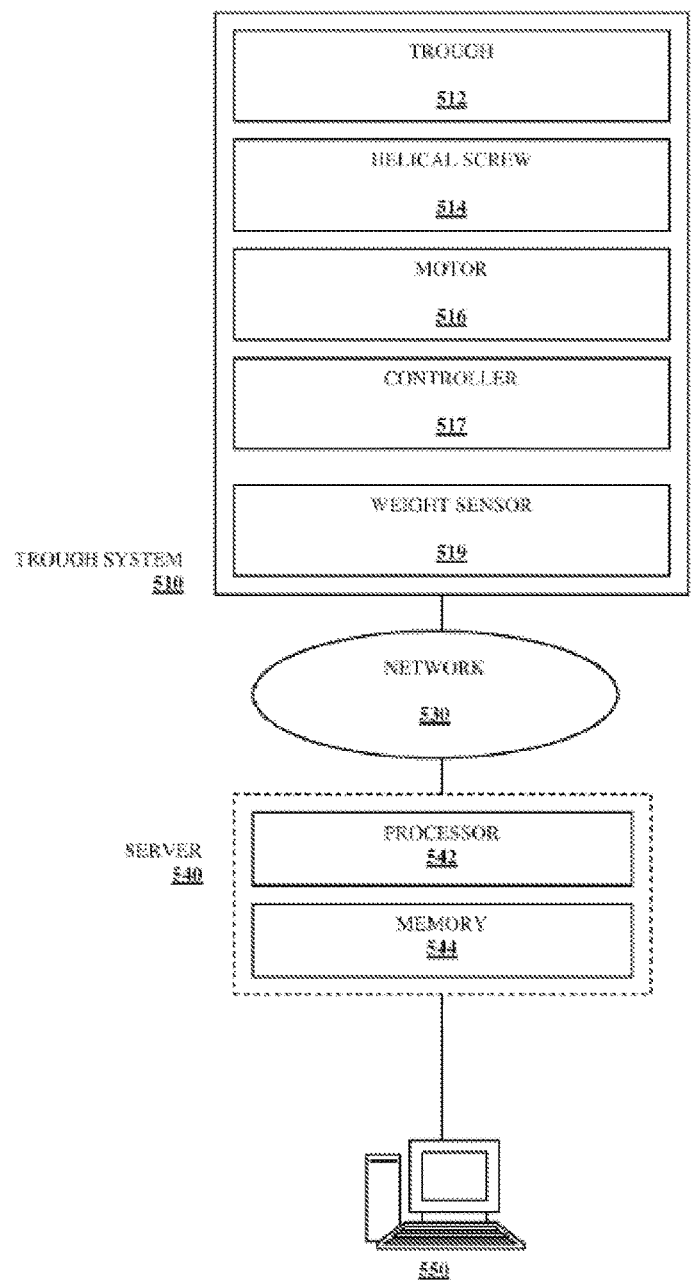
FIG. 5 is a schematic diagram illustrating a system of an embodiment for effecting the methods described herein.

FIG. 5 illustrates a system of an embodiment for effecting the methods described above. Trough system 510 transmits and receives data via network 530 to a server 540. According to some embodiments, trough system 510 comprises trough 512, helical screw 514, motor 516, controller 517 and weight sensor 519, and can be, for example, the trough system illustrated in FIGS. 3, 4A and 4B herein.

Either or both of server 540 and user device 550 are computer systems. In embodiments in which server 540 is used, server 540 comprises processor 542 and memory 544, and may be an HTTP (Hypertext Transfer Protocol) server, such as an Apache server, or an FTP server. Memory 544 may be any type of volatile or non-volatile storage media that includes, for example, one or more of read-only memory (ROM), random access memory (RAM), magnetic disk storage media, optical storage media, flash memory devices, and zip drives.

When server 540 is used, user device 550 may be a simple receiver or display device capable of implementing visual and/or audio alarms, instead of a fully functional computer system. In either embodiment, user device 550 may comprise one or more of analog or digital interfaces, mainframes, minicomputers, personal computers, laptops, personal digital assistants (PDAs), cell phones, televisions, audio receivers, video receivers, displays, and the like.

Server 540 and user device 550 are characterized in that they are capable of being connected to network 530. Network 530 may be any network for transmitting and receiving data to and/or from trough system 510, for transmitting and receiving data to and/or from server 540, and for transmitting and receiving data to and/or from user device 550. For example, network 530 may be a local area network (LAN), wide area network (WAN), a telephone network, such as the Public Switched Telephone Network (PSTN), an intranet, the Internet, or combinations thereof. In other embodiments, network 530 may be a telemetry network, such as one or more of a mud pulse telemetry network, an electromagnetic telemetry network, a wired pipe network, a pipe-in-pipe network, an acoustic telemetry network, a torsion telemetry network, or combinations thereof. In still other embodiments, network 530 can be a combination of traditional and telemetry networks.

In use, trough system 510 measures the weight of the system using weight sensor 519, and transmits the measurement to server 540 over network 530. Trough system 510 also measures the torque required by motor 516 to maintain a constant-rate rotation of helical screw 514 through the cuttings via a torque meter within controller 517, and transmits this measurement to server 540 over network 530. These measurements can be made and transmitted constantly, without interruption, in real time. Alternatively, these measurements can be made on demand, at predetermined times, at predetermined intervals, at random times, or based on the performance of one or more conditions.

Although illustrated and described herein with respect to a torque meter, any of a number of other methods or devices can be used to measure or estimate torque in accordance with embodiments of the invention. For example, if motor 516 is an electric motor, the electrical power used to run motor 516 can be measured to indicate the torque required to drive helical screw 514 at a constant speed. If motor 516 is a hydraulic or pneumatic motor, the change in pressure of the fluid driving helical screw 514 at a constant speed can be measured to indicate the torque required.

According to some embodiments, server 540 decodes the data received from trough system 510, if necessary, and converts it into a format usable by processor 542, memory 544 and/or user device 550. In an embodiment of the invention using a wired pipe network as network 530, server 540 is again not necessarily required, and data can be transmitted directly to and from network 530 and user device 550. In this embodiment, user device 550 can convert the electrical data signal received from network 530 into decodable computer-readable signals.

In embodiments where server 540 is used, server 540 can be directly wired, wirelessly connected, or a combination thereof, to trough system 510. In one embodiment, server 540 acts merely as a receiver for user device 550 using, for example, antennas, acoustic receivers, pipe-in-pipe electrical connections, wires, etc., and can convert an electrical data signal received from network 530 into decodable computer-readable signals.

Although described herein with respect to server 540, it is understood that trough system 510 may alternatively transmit and receive data directly to and from at least one user device 550, and server 540 can be eliminated entirely. In embodiments in which server 540 is not used, user device 550 may itself include a processor and memory to perform the functions described herein with respect to server 540.

According to some embodiments, processor 542 of server 540 retrieves from memory 544 stored data relating to the torque required to maintain constant rotation of helical screw 514 through natural cuttings, i.e., cuttings without any drilling fluid present. This "natural cuttings" data can initially be established by measuring the torque required to maintain rotation of helical screw 514 at a particular speed through known volumes, weights and densities of natural cuttings, and stored in memory 544. The data points can then be plotted onto a graph, a curve can be fit to the points, and additional data points beyond the range of the collected data can be extrapolated. Data charts and equations representing this relationship can also be established.

According to some embodiments, processor 542 compares the measured torque required to maintain constant rotation of helical screw 514 through the cuttings in trough 512, to the known torque required to maintain the same constant rotation of helical screw 514 through natural cuttings. Using a graph, chart or equation illustrating a known ratio or percentage of fluid to cuttings based on the difference in torque, processor 542 estimates the amount of drilling fluid on the cuttings, and the amount of cuttings themselves, within trough 512.

According to some embodiments, when the discharged cuttings are measured within trough 512, processor 542 corrects the measured weight of the cuttings to account for the weight of trough 512, helical screw 514, motor 516, torsion meter 517, weight sensor 519, and any other components attached to trough system 510 and affecting its weight (other than the cuttings). Processor 542 then estimates the weight of the natural cuttings within the trough (i.e., cuttings without any residual drilling fluid), such as by multiplying the percentage of cuttings in the discharge by the measured weight of the discharged cuttings.

According to some embodiments, processor 542 retrieves from memory 544 an expected or predicted volume of cuttings to be discharged from the shakers. Such predictions can be obtained, for example, from the volumetric lag tables produced by the InSite® software package from Halliburton Energy Services Inc. According to some embodiments, processor 542 further retrieves from memory 544 the density of the discharged cuttings, then calculates the expected or predicted weight of the natural cuttings being discharged into the trough.

Processor 542 compares the actual weight of the natural cuttings within the trough to the expected weight of cuttings discharged from the shakers, and retrieves an acceptable range of differences or tolerances from memory 544. This difference between estimated and predicted weights, along with other measurements and estimations relating to the cuttings in the trough (e.g., measured torque, weight of cuttings, estimated volume of drilling fluid on the discharged cuttings, estimated volume of natural cuttings) are stored in memory 544, as well as any other relevant or associated data, such as downhole conditions, drilling parameters, environmental conditions, date and time, operator, etc. Although described herein with respect to estimated and predicted weights of cuttings, it is understood that other parameters may be used with similar results, such as estimated and predicted percentages of cuttings per volume of drilling fluid, estimated and predicted volumes of cuttings, etc.

According to some embodiments, if the estimated and predicted volumes differ by more than an acceptable amount, server 540 sends a signal to user device 550, which, in turn, activates an alarm or another visual or audible indicator. In another embodiment, if the percentage of fluid on the discharged cuttings is higher than an acceptable threshold, server 540 can also send a signal to user device 550, which, in turn, activates an alarm or another visual or audible indicator.

In either embodiment, server 540 can further transmit all measured, estimated and predicted data to user device 550. For example, an operator at user device 550 can assess the data in conjunction with other relevant information (such as downhole conditions), and choose and implement appropriate remedial or corrective actions, if desired. In another embodiment, user device 550 can analyze the data in conjunction with other relevant available data, and automatically select and implement appropriate remedial actions. In still another embodiment, user device 550 can analyze the data in conjunction with other relevant available data, and suggest one or more appropriate remedial actions to the operator, who must, in turn, implement the desired actions.

Optionally, the measured, estimated and predicted data can further be stored in conjunction with the previously-referenced "natural cuttings" data, and plotted onto the graph. A new curve can then be fit to the data points to further refine the graph, and additional data points beyond the range of the collected data can more accurately be extrapolated. Similarly, a data chart or equation can be updated based on the new data.

Further, a graph of the torque required to drive the helical screw through the cuttings in the trough versus the percentage of fluid on the cuttings can be built up and refined using tried and true methods. For example, the above-described methods can be further refined for future use and reference by measuring and accounting for (A) the density of the drilling fluid at the time of measurement, (B) the density of the cuttings coming out of the borehole at the time of measurement, and (C) the density of the mixture at the time of measurement. In any case, the constant, real-time reading of power or torque can be calibrated and used as a real-time indicator of the amount of drilling fluid on the cuttings, eliminating the need for spot checks. Further, because the amount of drilling fluid that remains on cuttings can vary significantly, the accuracy of the readings is increased through constant measurement, as estimations between spot check measurements become unnecessary.

By determining the amount of drilling fluid remaining on cuttings, the loss of drilling fluid due to carryover, which can be substantial, can be tracked and accounted for. Further, by removing the estimated weight of remaining drilling fluid from the estimated weight of discharged cuttings, a better assessment can be made of the amount of cuttings coming over the shakers. By more accurately estimating the amount of returned cuttings and determining whether it is as expected, any build up of cuttings in the annulus can be detected earlier to prevent a number of problems, such as twist-offs and pipe sticking, that can lead to catastrophic failure. In addition, the flow rate and density of the drilling fluid can be adjusted and optimized to ensure efficient removal of cuttings from the annulus.

Although described with respect to the method illustrated in FIG. 2, it is understood that any of the methods or any portions thereof that are described herein can be similarly performed. Further, although described with particular devices, it is understood that a variety of similar devices may be employed to perform the processes described herein. Various functions of these and other embodiments can be described as modules of computer executable instructions recorded on tangible media. The modules can be segregated in various manners over various devices.

Figure 6:
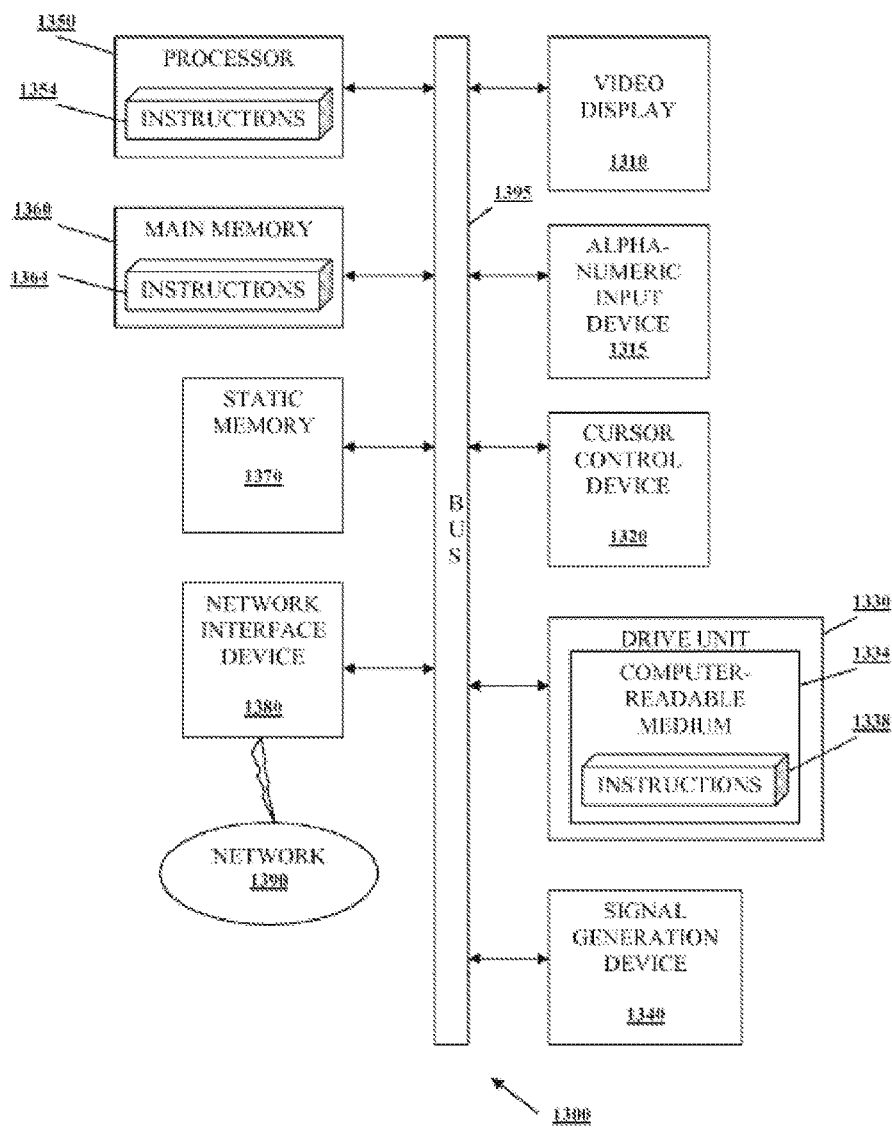
FIG. 6 is diagrammatic representation of a machine having a set of instructions for causing the machine to perform any of the one or more methodologies discussed herein.

FIG. 6 shows a diagrammatic representation of a machine in the exemplary form of computer system 1300 within which a set of instructions, for causing the machine and/or slave devices to perform any of the one or more methodologies discussed herein, may be executed. In alternative embodiments, the machine operates as a standalone device or may be connected (e.g., networked) to other machines. In a networked deployment, the machine may operate in the capacity of, for example, a server or a client machine in server-client network environment, or as a peer machine in a peer-to-peer (or distributed) network environment. The machine may be, for example, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

According to some embodiments, computer system 1300 comprises processor 1350 (e.g., a central processing unit (CPU), a graphics processing unit (GPU) or both), main memory 1360 (e.g., read only memory (ROM), flash memory, dynamic random access memory (DRAM) such as synchronous DRAM (SDRAM) or Rambus DRAM (RDRAM), etc.) and/or static memory 1370 (e.g., flash memory, static random access memory (SRAM), etc.), which communicate with each other via bus 1395.

According to some embodiments, computer system 1300 may further comprise video display unit 1310 (e.g., a liquid crystal display (LCD) or a cathode ray tube (CRT)). According to some embodiments, computer system 1300 also may comprise alphanumeric input device 1315 (e.g., a keyboard), cursor control device 1320 (e.g., a mouse), disk drive unit 1330, signal generation device 1340 (e.g., a speaker), and/or network interface device 1380.

Disk drive unit 1330 includes computer-readable medium 1334 on which is stored one or more sets of instructions (e.g., software 1338) embodying any one or more of the methodologies or functions described herein. Software 1338 may also reside, completely or at least partially, within main memory 1360 and/or within processor 1350 during execution thereof by computer system 1300, main memory 1360 and processor 1350 also constituting computer-readable media. Software 1338 may further be transmitted or received over network 1390 via network interface device 1380.

While computer-readable medium 1334 is shown in an exemplary embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding or carrying a set of instructions for execution by the machine and that cause the machine to perform any one or more of the methodologies of the present invention. The term "computer-readable medium" shall accordingly be taken to include, but not be limited to, solid-state memories, and optical and magnetic media.

It should be understood that processes and techniques described herein are not inherently related to any particular apparatus and may be implemented by any suitable combination of components. Further, various types of general purpose devices may be used in accordance with the teachings described herein. It may also prove advantageous to construct a specialized apparatus to perform the methods described herein. Those skilled in the art will appreciate that many different combinations of hardware, software, and firmware will be suitable for practicing the present invention.

The present invention has been described in relation to particular examples, which are intended in all respects to be illustrative rather than restrictive. Further, while the present invention has been described in connection with a number of exemplary embodiments, and implementations, the present inventions are not so limited, but rather cover various modifications, and equivalent arrangements.

Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A method for improved cuttings measurements in drilling operations, the method comprising:
   rotating a helical screw in a trough at a first speed;
   measuring a first weight of a cuttings mixture within the trough;
   measuring a first torque required to maintain rotation of the helical screw at the first speed through the cuttings mixture;
   calculating a difference between the first torque and a second torque required to maintain rotation of the helical screw at the first speed through a second weight of natural cuttings equal to the first weight.

2. The method of claim 1, wherein the cuttings mixture comprises at least one of drilling fluid and discharged cuttings.

3. The method of claim 2, further comprising:
   determining at least one of a percentage of the discharged cuttings in the cuttings mixture and a percentage of the drilling fluid in the cuttings mixture, using the difference between the first torque and the second torque.

4. The method of claim 3, further comprising:
   calculating a third weight of the discharged cuttings using the first weight and the percentage of the discharged cuttings in the cuttings mixture.

5. The method of claim 4, further comprising:
   determining a fourth weight of predicted cuttings output.

6. The method of claim 5, further comprising:
   comparing the third weight to the fourth weight.

7. The method of claim 6, wherein an alarm is activated if the third weight does not equal the fourth weight.

8. The method of claim 3, further comprising:
   comparing the percentage of the drilling fluid in the cuttings mixture to a threshold percentage.

9. The method of claim 8, wherein an alarm is activated if the percentage of the drilling fluid is greater than the threshold percentage.

10. A system for improved cuttings measurements in drilling operations, the system comprising:
    a trough;
    a helical screw in the trough;
    a motor that rotates the helical screw within the trough at a first speed;
    a weight sensor that measures a first weight of the trough; and
    a torque meter that measures a first torque required to maintain rotation of the helical screw at the first speed.

11. The system of claim 10,
    wherein the trough comprises a cuttings mixture, and
    wherein the cuttings mixture comprises at least one of drilling fluid and discharged cuttings.

12. The system of claim 11, further comprising:
    a processor that:
    calculates a second weight of the cuttings mixture using the first weight of the trough; and
    calculates a difference between the first torque and a second torque required to maintain rotation of the helical screw at the first speed through a third weight of natural cuttings equal to the second weight; and
    a memory coupled to the processor.

13. The system of claim 12, wherein the processor further determines at least one of a percentage of the discharged cuttings in the cuttings mixture and a percentage of the drilling fluid in the cuttings mixture, using the difference between first torque and the second torque.

14. The system of claim 13, wherein the processor further calculates a fourth weight of the discharged cuttings using the second weight and the percentage of the discharged cuttings in the cuttings mixture.

15. The system of claim 14, wherein the processor further determines a fifth weight of predicted cuttings output.

16. The system of claim 15, wherein the processor further compares the fourth weight to the fifth weight.

17. The system of claim 16, further comprising:
    an alarm that activates if the fourth weight does not equal the fifth weight.

18. The system of claim 13, wherein the processor further compares the percentage of the drilling fluid in the cuttings mixture to a threshold percentage.

19. The system of claim 18, further comprising:
    an alarm that activates if the percentage of the drilling fluid is greater than the threshold percentage.

* * * * *